United States Patent [19]

Goodhue et al.

[11] 4,276,377
[45] Jun. 30, 1981

[54] CREATININE IMINOHYDROLASE FREE FROM UREASE ACTIVITY

[75] Inventors: Charles T. Goodhue, Rochester; Theodore W. Esders; Prakash S. Masurekar, both of Webster, all of N.Y.

[73] Assignee: Eastman Kodak Company, Rochester, N.Y.

[21] Appl. No.: 91,218

[22] Filed: Nov. 5, 1979

[51] Int. Cl.³ .......................... C12Q 1/34; C12N 9/78
[52] U.S. Cl. ..................................... 435/18; 435/227; 435/850
[58] Field of Search ................................. 435/18, 227

[56] References Cited

U.S. PATENT DOCUMENTS

| | | | |
|---|---|---|---|
| 3,806,420 | 4/1974 | Holz et al. | 435/816 X |
| 3,907,644 | 9/1975 | Mollering et al. | 435/227 X |
| 4,039,384 | 8/1977 | Suzuki et al. | 435/227 |
| 4,087,329 | 5/1978 | Terada et al. | 435/227 |

OTHER PUBLICATIONS

Szulmajster, Journal of Bacteriology, vol. 75, pp. 633-639 (1958).
Szulmajster, Biochem. Biophys. Acta, vol. 30, pp. 154-163 (1958).

Primary Examiner—Lionel M. Shapiro
Attorney, Agent, or Firm—J. Jeffrey Hawley

[57] ABSTRACT

A urease-free creatinine iminohydrolase enzyme preparation obtained from an aerobic soil microorganism. The enzyme of the preparation preferably has a molecular weight of from about 250,000 to 300,000; a maximum activity at a pH between 7 and 8 as measured at 37° C.; a $K_m$ of about 3 to 5 mM for creatinine as measured at 37° C., pH 7.5; and a specific activity for creatinine of at least about 1.0 unit per milligram of protein in the preparation as measured at 37° C., pH 7.5. The preferred enzyme preparation is derived from the aerobic soil microorganism ATCC 31,546. Assay methods, compositions, and elements containing the aforementioned urease-free creatinine iminohydrolase for the determination of creatinine in an aqueous liquid are also disclosed.

38 Claims, No Drawings

CREATININE IMINOHYDROLASE FREE FROM UREASE ACTIVITY

FIELD OF THE INVENTION

This invention relates to urease-free creatinine iminohydrolase. Assay methods, compositions, and elements containing urease-free creatinine iminohydrolase are also disclosed for the analysis of aqueous liquids containing creatinine.

BACKGROUND OF THE INVENTION

Creatinine is a metabolic product produced by degradation of both creatine and phosphorcreatine. Creatinine is found in both the blood and urine. It is ultimately excreted in the urine at a relatively constant rate. Creatinine levels in the body fluids represent a highly useful indicator of renal disease and certain muscular diseases. Normal concentrations of creatinine in blood serum typically are within the range of from about 0.5 to about 1.7 mg per 100 ml of serum.

Creatinine iminohydrolase is an enzyme which specifically catalyzes the hydrolysis of creatinine to ammonia. Accordingly, by contacting an aqueous liquid containing creatinine with this enzyme to generate ammonia, the presence and/or concentration of creatinine in the liquid can be determined by detecting the level of generated ammonia. This enzyme can therefore play an important role in the clinical laboratory where it can be used as a diagnostic test reagent for the determination of creatinine in biological liquids.

Creatinine iminohydrolase, sometimes referred to as creatinine desimidase, has heretofore been obtained from various microorganisms. For example, J. Szulmajster, in *J. Bacteriol*, 75: 633, 1958 and *Biochim Biophys Acta*, 30: 154, 1958 describes a preparation of creatinine iminohydrolase from an anaerobic, gram-positive microorganism *Clostridium paraputrificum*. In addition, U.S. Pat. No. 4,087,329 and 4,134,793 describe the production of creatine iminohydrolase from several aerobic sources including microorganisms from the genera Brevibacterium, Corynebacterium, Pseudomonas and Arthrobacter. Also, Thompson and Rechnitz, *Analytical Chemistry*, Vol. 46, No. 2, February, 1974 at p. 246 describe a creatinine iminohydrolase enzyme obtained from Beckman Inc., Microbics Operations, LaHabra, California and the use of this enzyme to assay for creatinine.

In the production of creatinine iminohydrolase from a microorganism source, the desired enzyme is generally extracted from the microbial cells or the nutrient medium in which the cells are cultured together with various other enzymes capable of producing ammonia, particularly urease. Urease contamination of creatinine iminohydrolase enzyme preparations presents a serious problem because both urea, the substrate for urease, and creatinine, the substrate for creatinine iminohydrolase, are typically present in serum and other biological fluids. Moreover, urea is typically present in serum in much greater concentration than creatinine. Thus, an enzymatic assay of serum creatinine by use of a creatinine iminohydrolase enzyme preparation contaminated with urease leads to significant assay error through the production of spurious amounts of ammonia.

To overcome the urease contamination problem, creatinine iminohydrolase preparations must typically undergo extensive purification procedures to remove the urease contaminant. This is specifically noted, for example, at page 248 of the aforementioned Thompson and Rechnitz publication. In their publication, Thompson and Rechnitz recommend the use of ion exchange chromatography using DEAE cellulose beads (available from Pharmacia, Uppsala, Sweden) to purify the enzyme. Similarly, the aforementioned U.S. Pat. Nos. 4,087,329 and 4,134,793 also employ ion exchange chromatography using DEAE cellulose beads to remove protein contaminants, presumably enzyme contaminants, from the crude creatinine desimidase preparations described in these patents. Accordingly, the discovery of a urease-free creatinine iminohydrolase enzyme preparation would represent a particularly valuable contribution to the art.

RELATED APPLICATIONS

Masurekar U.S. patent application Ser. No. 091,216 filed concurrently herewith entitled "Process And Nutrient Medium For Growing Microorganism" describes and claims a fermentation process and improved nutrient medium for production of creatinine iminohydrolase from an aerobic soil microorganism such as ATCC 31, 546.

McCollough, Esders and Lynn, U.S. patent application Ser. No. 091,217 filed concurrently herewith entitled "Process For The Recovery Of Intracellular Enzymes" describes and claims an improved method for the extraction of intracellular enzymes such as urease-free creatinine iminohydrolase from the aerobic soil microorganism ATCC 31,546.

Both of the foregoing patent applications are expressly incorporated by reference herein.

SUMMARY OF THE INVENTION

The present invention provides a urease-free creatinine iminohydrolase enzyme preparation. This enzyme preparation is obtained from an aerobic soil microorganism. The desired urease-free creatinine iminohydrolase enzyme preparation is obtained by a method comprising the steps of growing an aerobic soil microorganism such as the aerobic soil microorganism ATCC 31, 546 in a nutrient medium to produce urease-free creatinine iminohydrolase and extracting the urease-free creatinine iminohydrolase from the microorganism Even in crude form, the creatinine iminohydrolase enzyme preparation of the present invention is free from urease contamination. Accordingly, as defined herein, a urease-free enzyme preparation refers to an enzyme preparation that in crude, unpurified form as extracted and separated from the microbial cells in which it was produced exhibits substantially no urease activity. A typical assay procedure for determining urease activity is described hereinafter in Example 2B.

A further embodiment of the invention provides a method, assay composition, and an element for the determination of creatinine contained in an aqueous liquid by contacting together the liquid and the above-described urease-free creatinine iminohydrolase enzyme preparation to produce a detectable amount of ammonia. This liquid analysis method is particularly useful for aqueous liquids which contain both urea and creatinine because the effective absence of urease activity in the creatinine iminohydrolase enzyme preparation eliminates urea as an interferent.

An especially preferred embodiment provides an assay composition for determination of creatinine, and an assay element containing this composition, the assay composition comprising the urease-free creatinine iminohydrolase enzyme preparation and an ammonia detector. Preferably, the ammonia detector is a chromogenic indicator which undergoes a change in color in the presence of ammonia.

DETAILED DESCRIPTION OF THE INVENTION

According to the present invention, a urease-free creatinine iminohydrolase enzyme preparation is obtained from an aerobic soil microorganism. A preferred culture providing useful levels of such urease-free creatinine iminohydrolase is designated ATCC 31,546 based on its deposit with the American Type Culture Collection, Rockville, Md. 20852.

A taxonomic identification of the preferred aerobic soil microorganisms such as the ATCC 31,546 microorganism is as follows: Using a laboratory microscope at a magnification of 1000 X, an isolate of the microorganism cultured aerobically on a "CFM" nutrient medium, described hereinafter, is gram-negative and contains single cells appearing as small rods having a size of about 0.3–0.5 by 2–4 microns, though long 40 microns are typically present. Motility by flagella, possibly degenerate peritrichous flagella or polar flagella, is sometimes observed. The isolate forms translucent, yellow colonies of varying sizes. The isolate hydrolyzes gelatin and grows on glucose although carbohydrate metabolism, in general, is poor. Vegetable proteins are superior to animal proteins as nitrogen sources for the isolate.

When subjected to conventional biochemical tests, the above-noted isolate cultured on CFM nutrient medium is further characterized as follows:
O-nitrophenylglycoside: Negative
Arginine dihydrolase: Negative
Lysine decarboxylase: Negative
Ornithine decarboxylase: Negative
Citrate: Positive
Urea: Negative
Tryptophan deaminase: Negative
Indole not produced
Voges-Proskauer test: Negative
$H_2S$ not produced
Phenylalanine: Negative
Malonate: Negative
Esculin: Negative
Acid but no gas from galactose.
Neither acid nor gas from adonitol, dulcitol, lactose, levulose, maltose, mannose, raffinose, salicin, inositol, trehalose, sorbitol, glycerol, starch, glucose, cellulose, and xylose.
Nitrate reduction: Positive
Nitrate respiration: Negative The foregoing biochemical tests carried out on the isolate cultured on the CFM nutrient medium were performed as described by Blair et al, "Manual of Chemical Microbiology", Williams and Wilkins Company, Baltimore, Maryland, 1970. On the basis of the foregoing taxonomic and biochemical tests the preferred microorganism is tentatively assigned to the genus Flavobacterium and given the species name *filamentosum*.

Unexpectedly, the creatinine iminohydrolase enzyme preparation extracted from an aerobic soil microorganism such as ATCC 31,546 is free of urease activity, even in an unpurified state. The urease-free creatinine iminohydrolase enzyme preparation is further characterized by the following properties:

The enzyme of the preparation is a protein having a molecular weight of about 250,000 to 300,000 as measured by gel filtration using Sephadex G-200 gel (available from Pharmacia, Uppsala, Sweden) or by sucrose gradient centrifugation. The enzyme exhibits enzymatic activity over a pH range of from about 6 to 10 and a temperature range of from about 25° to 45° C. and has a maximum enzyme activity at a pH between about 7 and 8 in the presence of dipotassium hydrogen phosphate buffer. The enzyme has a Michaelis constant, $K_m$, of about 3 to 5 mM as measured at 37° C. and a pH of about 7.5. The urease-free creatinine iminohydrolase enzyme preparation obtained in crude, unpurified form typically exhibits a specific activity for creatinine of at least about 0.1 unit per milligram of protein in the enzyme preparation. One unit of creatinine activity is defined herein as that amount of enzyme which will catalyze the conversion of 1 $\mu$mole of creatinine to 1 $\mu$mole of ammonia per minute at 37° C. and a pH of about 7.5. The specific activity of the enzyme preparation for creatinine can be increased by purification as described in further detail hereinafter to provide a specific activity for creatinine of at least about 1.0, preferably in excess of 2.5, units per mg of protein in the enzyme preparation.

The aqueous nutrient medium on which microorganisms which produce urease-free creatinine iminohydrolase are grown has a pH in the range of from about 5.0 to 10.0, and comprises:
(i) a carbon source comprising an amino acid precursor representing an organic free from amino groups,
(ii) a nitrogen source comprising creatinine,
(iii) trace nutrients, and
(iv) a buffer.

The amino acid precursors serving as carbon sources represent organic acids free from amino groups. Amino acid precursors refer herein to both "direct" and "indirect" precursors for amino acids. A direct precursor represents a substance which is one metabolic reaction step removed from an amino acid, whereas an indirect precursor requires two metabolic reaction steps to form an amino acid. Thus, for example, fumaric acid represents a "direct" amino acid precursor as it can be metabolically converted to the amino acid aspartic acid in a single reaction step; whereas lactic acid represents an "indirect" amino acid precursor as it must first be metabolically converted to pyruvic acid (a direct amino acid precursor) which can then be metabolically converted to alanine. Direct amino acid precursors are preferred over indirect amino acid precursors.

The amino acid precursors employed in the aqueous nutrient medium are further characterized as organic acids free from amino groups. A partial listing of preferred such organic acids which are direct amino acid precursors includes fumaric acid, α-ketoglutaric acid, and pyruvic acid. A partial listing of useful such organic acids which are indirect amino acid precursors includes lactic acid, malic acid, citric acid, and succinic acid.

The amount of the above-described amino acid precursor employed as a carbon source can vary. Useful amounts have typically been found to be in the range of from 1.0 to 20.0 grams per liter of the aqueous nutrient medium, preferably in the range of from 5.0 to 10.0 grams per liter.

The trace nutrients contained in the aqueous medium include water-soluble inorganic salts. Yeast extract can also be present. Typically these trace nutrients are added in small quantities in an amount effective to promote cell growth of the microorganism and increased yield of enzyme from the microorgaism. Typically, a useful amount of yeast extract is within the range of from about 0.1 gram to 2 grams per liter of the nutrient medium, preferably from about 0.5 to 1.5 grams per liter.

Typical water-soluble inorganic salts which can be present as trace nutrients include water-soluble salts of phosphorous, magnesium, calcium, iron, manganese, zinc, sodium, and other water-soluble salts, the cationic component thereof typically being selected from Periods 3 and 4 of the Periodic Table of the Elements. Preferably, a mixture of several different inorganic salts are present as trace nutrients.

The aqueous nutrient medium also contains a buffer. Preferably, the buffer is a phosphorous-containing buffer such as a phosphate buffer. In this preferred case, the buffer not only serves as a buffer but also serves as a trace phosphorous source for the microorganism. A preferred phosphate buffer is dipotassium hydrogen phosphate, $K_2HPO_4$, typically present in an amount within the range of from about 3.0 to 10.0 grams per liter, preferably 3.0 to 6.0 grams per liter.

The pH of the aqueous nutrient medium is typically maintained in a range of from about 5.0 to 10.0, preferably about 6.0 to 7.5. The pH of the medium can readily be adjusted to a value in the aforementioned range by addition of a base such as KOH or NaOH, preferably NaOH. The pH is then maintained within this range by the presence of the above-noted buffer.

Because the above-noted soil microorganism which is grown in the improved aqueous medium is aerobic, an oxygen supply sufficient to achieve maximum cellular growth of and enzyme production by the microorganism is necessary. In general, the optimum quantity and method of oxygen delivery to a given volume of a specific medium can readily be determined by routine testing familiar to those skilled in the art whereby the cell growth and enzyme production levels of the microorganism are monitored while the oxygen supply to the medium is varied. The optimum amount of oxygen supply as determined by the mass transfer coefficient can then readily be chosen on the basis of maximizing cell growth and enzyme production, with maximum enzyme production being the controlling factor.

A useful aqueous nutrient medium for cultivating useful aerobic soil microorganisms such as ATCC 31,546, identified hereinabove as a "CFM" medium consists of the following nutrients, the specified concentration based on one liter of water:

| | |
|---|---|
| $K_2HPO_4$ | 2.0 g |
| Creatinine: | 5.0 g |
| Fumaric acid: | 2.0 g |
| Agar, if desired: | 2.0 g |
| Yeast extract, if desired: | 1.0 g |
| Salt solution: | 10.0 ml |

The above-noted salt solution consists of the following salts dissolved in 0.1 N HCl, the specified concentrations based on one liter of 0.1 N HCl:

| | |
|---|---|
| $MgSO_4$: | 12.2 g |
| $CaCl_2 . 2H_2O$: | 0.076 g |
| $MnSO_4 . H_2O$: | 1.7 g |
| $FeSO_4 . 7H_2O$: | 2.8 g |
| $ZnSO_4 . 7H_2O$: | 0.06 g |
| NaCl: | 0.6 g |
| $NaMoO_4 . 2H_2O$: | 0.1 g |

The above-identified CFM nutrient medium, optionally containing agar and yeast extract, is typically adjusted to a pH of about 7 using NaOH or KOH and then sterilized by autoclaving prior to growth of the microorganism thereon. Culturing the preferred aerobic soil microorganism in this nutrient medium can be carried out at a temperature of about 15° to 42° C., preferably 25° to 30° C., to obtain production of the desired bacterial cells. Of course, this CFM nutrient medium may be adjusted and modified by those skilled in the art to further optimize the production of urease-free creatinine iminohydrolase. For example, an improved aqueous nutrient medium for growth of the aerobic soil microorganism ATCC 31,546 and improved production of urease-free creatinine iminohydrolase is described in the related Masurekar application noted hereinabove. The optimized nutrient medium described in the Masurekar application contains glucose as an additional carbon source and a vegetable protein hydrolysate or a non-peptic milk protein hydrolysate as an additional nitrogen source.

After the desired bacterial cells are grown by culturing the microorganism in a nutrient medium, they can be separated from the fermentation broth by centrifugation or other suitable means. Yields of from about 8 to 12 grams of cells (wet weight) per liter of CFM growth medium have been obtained.

Creatinine iminohydrolase, which is produced intracellularly by the microorganism can then be recovered by disrupting the cells and separating the enzyme from the cell debris. The resultant creatinine iminohydrolase as extracted from the cells and without further purification is free from urease activity.

To disrupt the cells, the cells are suspended in cold aqueous buffer at a concentration of about 15 to 20% (wet weight) and sonicated using an ultrasonic probe. The buffer is typically present at a concentration of about 0.1 M and the extraction can be carried out successfully at a pH of about 7.5, although higher or lower pH levels can also be used. The cold buffer suspension of the cells can be achieved by cooling the suspension in a brine-ice bath. The disrupted cells can then be centrifuged to remove cell debris. The urease-free creatinine iminohydrolase extracted from the disrupted cells can, if necessary or desired, be further purified by conventional techniques, such as organic solvent fractional precipitation, to increase the specific activiity of the enzyme.

Purification by organic solvent fractional precipitation is typically carried out at a low temperature, for example, within the range of from about 0° to about 15° C., using an organic solvent miscible in water but in which the enzyme precipitates at a specific solvent concentration. Typically, the water-miscible organic solvent is combined with unpurified urease-free creatinine iminohydrolase enzyme preparation extracted from the bacterial cells as described immediately hereinabove at a low temperature within the foregoing range using an ice bath. The concentration of the water miscible organic solvent initially combined with the enzyme preparation is typically within the range of from about 30 to 50 volume %, preferably 50 volume %, based on the amount of organic solvent and water present. A precipitate (containing undesired microbial protein) is obtained by addition of the organic solvent, and the supernatant containing the desired enzyme can then be separated by centrifugation. The organic solvent precipitation can then be continued to provide further purification. This can be done by combining additional solvent to the enzyme-containing supernatant to achieve an organic solvent concentration effective to precipitate the enzyme from the supernatant. This typically occurs at organic solvent concentration levels on the order of about 60 to 65 volume %.

Useful water-miscible organic solvents which can be employed in the organic solvent fractional precipitation process include acetone and alcohols such as n-propanol, isopropanol, t-butanol and ethanol. N-propanol is preferred.

The urease-free creatinine iminohydrolase, when extracted and purified by the foregoing organic solvent fractional precipitation procedure, typically exhibits a specific activity of at least about 1.0 unit per mg of protein in the enzyme preparation.

If desired, the above-described extraction and organic solvent fractional precipitation procedure can be modified as described in the McCollough, Esders and Lynn patent application noted hereinabove. In the McCollough, Esders and Lynn modification, the water-miscible organic solvent is introduced directly into an aqueous suspension containing the disrupted microbial cells prior to removal of any cell debris. This eliminates a separation step, stabilizes the enzyme during the recovery process, and increases the yield of the enzyme.

Further purification beyond organic solvent fractional precipitation can be carried out, if desired. However, because the creatinine iminohydrolase enzyme preparation is free from urease, extensive purification is often unnecessary. A purified form of the final enzyme preparation can be freeze-dried (sometimes referred to as lyophilization) for long-term storage. A powdered, urease-free creatinine iminohydrolase enzyme preparation is thus obtained.

Assay Compositions, Methods, and Elements

A preferred embodiment of the invention provides an assay composition, element, and method for the determination of creatinine in aqueous liquid. The assay composition comprises the urease-free creatinine iminohydrolase enzyme preparation and, preferably, one or more optional components such as an ammonia detector which undergoes a detectable change in response to a base such as ammonia (or ammonium ion) specifically. The assay method comprises:
 (a) contacting the assay composition with a creatinine-containing aqueous liquid sample at a pH and temperature effective for the composition to interact with creatinine and produce detectable amounts of ammonia (or ammonium ion) corresponding to the presence and/or concentration of creatinine; and
 (b) detecting said ammonia, for example, with the aforementioned detector.

Preferred ammonia detectors include chromogenic base indicators, that is substances which change color in the presence of a base such as ammonia. Typical chromogenic base indicators are bleachable dyes and dye precursors, both of which undergo a color change in the presence of a base. A typical chromogenic base indicator useful in the present invention is bromophenol blue. Other useful ammonia detectors are chromogenic ammonia specific indicators, that is, substances which change color in the presence of ammonia but not in the presence of other bases. Especially preferred chromogenic detectors are those having a molar extinction coefficient of 50,000 or more.

Base-bleachable dyes useful as chromogenic base indicators include styryl type dyes and pH-sensitive pyrilium dyes. Styryl type dyes are converted to a colorless species by breaking the conjugated chain of the dye in an alkaline medium. The color change undergone by a base-bleachable, pH-sensitive pyrylium dye proceeds by the elimination of the charged oxygen atom in the dye to form either a spiropyran or a pyridine.

The term "dye precursor" refers to compositions capable of forming a dye by (1) modification of molecular structure, for example, by elimination of one or more atoms such as in deprotonation, or by (2) combination with each other (autocoupling) or with a color coupler. Examples of the former include base-activatable chromogens, and examples of the latter include diazonium salts. Base-activated chromogens include protonated dyes, such as leuco cyanine dyes, nitro-substituted leuco dyes, and leuco phthalein dyes, which deprotonate to the dye form in the presence of a base. A partial listing of specific representative protonated dyes includes bromophenol blue, chlorophenol red, and other dyes such as disclosed in U.S. Pat. No. 3,929,760. Diazonium salts which form a dye in a basic environment such as provided by ammonia in the presence of a color coupler are well known in the art as useful dye formers.

A further description and listing of useful chromogenic base indicators including each of the types referred to hereinabove may be found by reference to U.S. Pat. No. 4,066,403 issued Jan. 3, 1978 and incorporated by reference herein.

Examples of chromogenic ammonia specific indicators which represent ammonia detectors useful in the assay compositions described herein include
 (a) diketones which condense with ammonia to produce a photometrically detectable dihydropyridine as described in Figures, Nelson and Sutton U.S. patent application Ser. No. 880,828 filed Feb. 24, 1978, now U.S. Pat. No. 4,176,008, issued Nov. 27, 1979, and
 (b) $\beta$-diketones which condense with ammonia in the presence of an aldehyde, preferably formaldehyde generated from a formaldehyde source, to produce a photometrically detectable substituted or unsubstituted dihydropyridine as described in Frank and Ponticello, U.S. Pat. application Ser. No. 880,827 filed Feb. 24, 1978, now U.S. Pat. No. 4,194,063, issued Mar. 18, 1980. Each of the aforementioned U.S. patent applications Ser. Nos. 880,828 and 880,827 are incorporated by reference herein.

If the particular ammonia detector employed in an assay composition of the invention is not specific to ammonia, for example, a pH-sensitive chromogen which changes color in the presence of ammonia or any other base, one must be careful to remove all bases, except for ammonia, from the presence of the detector. Otherwise, the presence of such other bases can lead to assay error. In many cases, this can readily be accomplished by contacting together the liquid sample to be assayed for creatinine with the urease-free creatinine iminohydrolase enzyme preparation under appropriate pH and temperature conditions to produce a detectable amount of ammonia, directing the fluid products of this enzymatic reaction through a barrier composition permeable to ammonia vapor but substantially impermeable to other liquid bases, e.g., liquids containing hydroxyl ions, and then contacting the ammonia-containing fluid which passes through the barrier composition together with the ammonia detector, e.g., a pH-sensitive chromogen.

Of course, other ammonia detectors such as various ammonia specific electrodes can also be employed. Such electrodes are described, for example, in Coleman, R., *Clin. Chem.* 18, 867 (1972). Still other ammonia detectors include enzymes which catalyze reactions specific for ammonia, for example, the glutamic dehydrogenase-catalyzed reaction using NADPH as the measurable substrate described hereinafter in Example 2A.

Preferably, a buffer is also present in the assay composition to maintain the pH during the assay within the effective pH range of the enzyme preparation. Phosphates such as tris(hydroxymethyl)aminomethanephosphate and dipotassium hydrogen phosphate are particularly suitable. However, other buffers may also be appropriate and are described, for example, by Good in *Biochemistry*, 5, 467 (1966).

The amounts of the various components of the assay composition can vary widely. Depending upon the range of creatinine concentrations for which the composition is intended, one uses more or less of the urease-free creatinine iminohydrolase enzyme preparation. When using the assay composition to analyze for creatinine concentrations varying from about 0 to about 20 milligrams per deciliter, one would typically employ an assay composition containing from about 1 to about 5 units of the enzyme preparation per ml of the reaction mixture.

Similarly, the amounts of ammonia detector and optional buffer employed in the assay composition can vary widely. Typically, the amount of buffer is an amount sufficient to maintain the pH of the assay composition during the assay within the effective pH range of the creatinine iminohydrolase enzyme. The amount of ammonia detector will depend essentially on the creatinine concentration for which the assay composition is intended.

A further embodiment of the invention provides a highly quantitative assay for the analysis of creatinine in an aqueous liquid. In this embodiment, free ammonia which can be present in the aqueous liquid is also assayed so that the concentration of such free ammonia can be effectively subtracted from the quantity of ammonia determined in the creatinine assay. Thus, the net ammonia determined in the creatinine assay represents only that which is produced by the urease-free creatinine iminohydrolase-catalyzed hydrolysis of creatinine to ammonia. In this embodiment, the assay method comprises:

(a) treating a first sample of the aqueous liquid to be assayed with an ammonia detector to produce a detectable change, e.g., a color change, corresponding to the amount of free ammonia contained in the sample; and (b) treating a second sample of the same aqueous liquid with a urease-free cretinine iminohydrolase-containing assay composition of the present invention to produce a detectable change corresponding to the amount of free ammonia in the second sample and the amount of ammonia generated by the creatinine iminohydrolase from the second sample, whereby the amount of ammonia detected in step (b) corrected for that detected in step (a) corresponds essentially only to that derived from the creatinine present in the aqueous liquid.

The assay composition and method of the invention for the analysis of creatinine in aqueous liquids can be employed in liquid analytical techniques. These are sometimes referred to as "wet chemistry" analytical techniques. The assay composition and methods described herein can also be employed in analytical techniques employing dry test elements, sometimes referred to as "dry chemistry" techniques.

In "wet chemistry" techniques, sometimes also referred to as solution assays, the assay is carried out entirely in a liquid medium; and the enzyme preparation or the assay composition containing it is typically combined with the liquid sample under analysis in a liquid medium. In such case, it is preferred to employ the enzyme preparation or assay composition in the aqueous medium at a temperature of from about 25° to about 45° C. and at a pH of from about 6 to about 10. If the ammonia detector is incorporated directly into the solution assay medium together with the creatinine iminohydrolase enzyme preparation, the ammonia detector function in a pH range which is compatible with that of the creatinine iminohydrolase enzyme preparation. Also, if other interfering bases are present in the solution assay medium, the ammonia detector should be ammonia specific. Alternatively, if the ammonia detector is separated from the liquid assay medium containing the creatinine iminohydrolase enzyme preparation by, for example, a barrier permeable to ammonia but impermeable to other liquid bases; the ammonia detector need not be ammonia specific and the pH of the detector need not be compatible with that of the enzyme preparation.

When the enzyme preparation and assay composition described herein are employed in "dry chemistry" techniques, they can be incorporated, for example, by imbibition, impregnation, or by coating techniques, into a reagent zone(s) of a dry test element, e.g., a reagent layer of a dip-and-read fibrous test strip or a reagent layer of a non-fibrous multilayer element as described in Przybylowicz et al U.S. Pat. No. 3,992,158 and Bruschi U.S. Pat. No. 4,066,403. In "dry chemistry" elements, the enzyme preparation or assay composition is typically present as a dry residue, for example, in a dry zone or layer of the test element.

It will be understood that when a "dry" chemistry analytical procedure is employed using the assay compositions of the present invention, interfering bases should be removed from the presence of the ammonia detector unless the detector is specific for ammonia. Thus, if the ammonia detector of the assay composition is base-sensitive (rather than ammonia specific), a typical dry chemistry test element will have the enzyme preparation of the assay composition located in one zone of the test element and the ammonia detector located in a separate zone of the element. A barrier composition permeable to ammonia but impermeable to other liquid bases is preferably interposed between the zone containing the enzyme and that containing the ammonia detector. As a result, ammonia generated in the enzyme reagent zone by the action of the enzyme on a creatinine-containing liquid sample will pass through the barrier composition to the base-sensitive ammonia detector. However, interferring liquid bases will be blocked by the barrier composition and therefore will not reach the base-sensitive ammonia detector.

A structure of a preferred dry chemistry analytical element having a spreading zone to distribute a sample of aqueous liquid to be assayed for creatinine, a reagent zone permeable to the liquid sample and containing a urease-free creatinine iminohydrolase enzyme preparation as described herein, a barrier zone selectively permeable to ammonia, and a separate ammonia detector zone suitable for non-specific base-sensitive detectors is described in Example 3 below.

The following non-limiting examples further illustrate the invention.

EXAMPLE 1

A. Growing Microorganism to Produce Urease-Free Creatinine Aminohydrolase

A sample from a slant of the aerobic soil microorganism ATCC 31,546 grown on the CFM nutrient medium (containing agar and yeast extract) described hereinabove for 2 days at 30° C. was transferred to a 250-ml flask containing 25 ml of the CFM (agar free) nutrient medium described hereinabove, adjusted to a pH of 7.0 with KOH. The cells were grown in the flask for 18–24 hours at 30° C. with shaking at 250 rpm and then transferred to a 2.8 l Fernbach flask containing 500 ml of the above-described CFM (agar free) nutrient medium. The cells were grown for 12–20 hours in the Fernbach flask at 30° C. with shaking at 150 rpm. The cells and the nutrient medium contained in 12 of the foregoing Fernbach flasks were then combined to form 6 liters of cells in nutrient medium. The cells from these 6 liters were then collected by centrifugation at 10,000 xg for 10 minutes and washed once with 1 liter of cold (about 4° C.) 0.1 M tris(hydroxymethyl)aminomethane-phosphate (tris-phosphate) aqueous buffer adjusted to a pH of 7.5. The yield was 10 g cells (wet weight) per liter nutrient medium. A 15–20 percent (w/v) suspension of these cells so obtained was then prepared in a 0.1 M tris-phosphate buffer adjusted to a pH of 7.5 and cooled using an ice-brine bath. To disrupt the cells, 100 ml aliquots of this cell suspension were sonicated for 6 minutes using a probe with standard tip (Ultrasonics, Inc. Plainview, New Jersey) powered by a Branson J-17A sonifier operating at a setting of 40 (Branson Sonic Power Company, Danville, Connecticut). The sonication was carried out in a Rosette cell suspended in a stirring ice-brine bath. The disrupted cells were centrifuged at 10,000 xg for 15 minutes at 4° C. to remove cell debris. From the total 6 liters of initial cell-containing CFM nutrient medium, a cell-free supernatant of about 500 to 600 ml was obtained. The creatinine iminohydrolase activity of this cell-free supernatant, as measured by the "GDH" assay described in Example 2 below, is reported in Table I.

B. Partial Purification of Creatinine Iminohydrolase

An equal volume of n-propanol cooled to −20° C. was added dropwise to the cell-free supernatant obtained as described in (A) above to bring the n-propanol concentration to 50 volume percent. The cell-free supernatant was stirred during addition of the n-propanol and was maintained at a low temperature in an ice bath. The final temperature of the supernatant at the completion of the addition of n-propanol was between 2° and 5° C. Thereafter, immediately on completion of n-propanol addition, a large proteinaceous precipitate was removed from the supernatant by centrifugation carried out at 10,000 xg at 4° C. for 15 minutes and discarded. The clear supernatant thus obtained was returned to a flask in the ice bath and one-half the original volume of n-propanol was added dropwise with stirring as described above to reach a concentration of n-propanol of 60 volume percent. This mixture maintained at 4° C. was subjected to centrifugation once again at 10,000 xg for 15 minutes. A precipitate in the form of a small pellet resulted containing the desired enzyme preparation. Removal of the supernatant liquid was accomplished by decantation, and the small pellet thus obtained was then resuspended in about 1/15 the original volume of supernatant with 0.1 M trisphosphate buffer adjusted to a pH of 7.5. This mixture was centrifuged at 10,000 xg for 10 minutes at 4° C. to clarify the urease-free creatinine iminohydrolase preparation. The specific activity of this creatinine iminohydrolase preparation, as determined by the "GDH" assay described in Example 2 below, is reported in Table I.

TABLE I

| Preparation and Purification of Creatinine Iminohydrolase | | |
|---|---|---|
|  | Cell-free Supernatant from (A) of Example 1 | Purified Enzyme Preparation from N-propanol Fractionation from (B) of Example 1 |
| Volume of Material | 600 ml | 41 ml |
| Total Units of Enzyme Activity | 1592 | 1147 |
| Specific Activity (U/mg) | 0.14 | 2.66 |
| Yield | 100% | 72% |
| Purification Factor | 1 | 19 |

EXAMPLE 2

Activity of Enzyme Preparation

A. Assay of Creatinine Iminohydrolase

To determine the creatinine iminohydrolase activity described in Example 1 above, an L-glutamic dehydrogenase, "GDH", assay method was employed. In the GDH assay method, production of ammonia from creatinine, which represents the activity of a creatinine iminohydrolase enzyme preparation, is measured using NADPH (nicotinamide-adenine dinucleotide phosphate, reduced form) in a GDH-catalyzed reaction as follows:

Creatinine is hydrolyzed to ammonia via the unknown activity of a creatinine iminohydrolase sample, and the resultant ammonia reacts with the reagent α-ketoglutaric acid in the presence of GDH as catalyst to produce glutamic acid. The latter reaction catalyzed by GDH uses the NADPH oxidation reaction (NADPH→NADP), the disappearance of the NADPH absorption peak at 340 nm providing the spectroscopically detectable means for monitoring the assay. That is, the rate of NADPH disappearance measures the rate of glutamic acid production which, in turn, measures the rate of ammonia production. The reaction mixture employed in the GDH assay method contained, in a total volume of one milliliter of 0.1 M N,N-bis(2-hydroxyethyl)glycine-KOH buffer solution having a pH of 7.6: 0.4 mg (ethylenedinitrilo) tetraacetic acid, disodium salt (Na$_2$EDTA), 1.6 mg α-ketoglutaric acid, 0.24 mg NADPH, 15 units GDH (ammonia-free), and 4.52 mg creatinine. One unit of GDH activity is defined as that amount of enzyme which catalyzes reduction of 1 μmole of α-ketoglutaric to glutamate per minute at pH 7.6 and 37° C. Reaction was initiated in the above-noted reaction mixture by addition of a small sample (about 2–10 milliunits) of the desired creatinine iminohydrolase enzyme preparation after equilibration of the reaction mixture at 37° C. Creatinine iminohydrolase activity was calculated by measuring the NADPH rate of disappearance at 340 nm (the molar extinction coefficient of NADPH at 340 nm being $6.22 \times 10^3$) in a spectrophotometer. One unit of enzyme activity was defined as that amount of enzyme necessary to catalyze the conversion of 1 μmole of creatinine to 1 μmole of ammonia per minute under the above-noted GDH assay reaction conditions.

(B) Assay of Urease and Enzyme Specificity

By substituting urea for the creatinine in the above-noted GDH assay method of (A), urease activity for the creatinine iminohydrolase enzyme preparation obtained from the procedure of Example 1 was determined. In this same manner, that is by substitution of creatinine with other potential enzyme substrates, including creatine, arginine, and guanidine, in the GDH assay method described in (A) of this example, the specificity of the creatinine iminohydrolase enzyme preparation obtained in Example 1 was also determined. Thus, the crude, unpurified creatinine iminohydrolase enzyme preparation represented by the cell-free supernatant obtained in (A) of Example 1 was determined to exhibit essentially no urease activity as shown in Table II below. In addition, this crude enzyme preparation obtained in (A) of Example 1 was found to be highly specific for creatinine as shown in Table II below. In Table II, the amount of the substrate substituted for the 4.52 mg of creatinine in the GDH assay method of (A) of this example is noted in terms of its mM concentration.

TABLE II

| Substrate Specificity of Creatinine Iminohydrolase | |
|---|---|
| Substrate | Units of Activity (using GDH assay) |
| creatinine (40 mM) | 25 |
| urea (100 mM) | 0.0 |
| creatine (20 mM) | 0.0 |
| arginine (100 mM) | 0.0 |
| guanidine (100 mM) | 0.0 |

EXAMPLE 3

Effect of Carbon Source

In this example, a series of tests was performed to evaluate various carbon sources for use in aqueous nutrient media to support cell growth and urease-free creatinine iminohydrolase enzyme production in the aerobic soil microorganism ATCC 31,546. In each test, the microorganism was transferred from an initial slant of the above-described CFM nutrient medium to a separate microbial growth medium and then to a final production medium. This fermentation process was conducted in accord with the fermentation process described in the Masurekar U.S. Patent Application noted hereinabove in "Related Applications". Each test was conducted in an identical manner, except that the carbon source in the final production medium was varied as described hereinafter. The specific procedure of conducting each test was as follows:

A fresh sample of the ATCC 31,546 culture was obtained by growing the microorganism for two days on a slant of the CFM medium (containing agar and yeast extract) at 25°–30° C. From this slant, a loopful of culture was inoculated into 25 ml of a microbial growth medium contained in a 250 Erlenmeyer flask. The microbial growth medium employed consisted of Tryp-Soy Broth, a "complex" medium composed of a vegetable protein hydrolysate sold by Scott Laboratories Inc., Fiskeville, R.I. Following inoculation of the culture into the Erlenmeyer flask, the flask was shaken at 200 rpm at 30° C. for eight hours to produce good growth without lysis of the microbial cells. Thereafter, a sample of the contents of the flask was microscopically inspected for culture purity and then aseptically centrifuged at 15,000 xg in a refrigerated centrifuge (available from DuPont Instruments, Newtown, Conn.) for 15 minutes to separate the cells from the Tryp-Soy Broth. The supernatant containing the Tryp-Soy Broth was discarded, and the solid material containing the precipitated microbial cells was then re-suspended in a volume of sterile distilled water equal to that present before centrifugation. 2 ml of this latter suspension was then used as an inoculum for a 250 ml Erlenmeyer flask containing 25 ml of a production medium to promote enzyme production by the microorganism. The specific composition of the production medium was varied as described hereinafter. However, in each case, once the microorganism was transferred as a 2-ml inoculum to the flask containing the particular production medium of interest, the flask was shaken at 30° C., 200 rpm for 10 hours. Thereafter, samples of the culture were withdrawn, diluted and dry-cell weight was determined. In addition, a 2.5 ml aliquot of the culture was centrifuged at 15,000 xg in a refrigerated centrifuge to separate the cells from the production medium. The supernatant containing the production medium was discarded. The precipitated cells were disrupted. Cell disruption was achieved as follows: 0.2 ml of an enzyme solution and 0.4 ml of cell suspension were added to 1.4 ml of 0.05 M tris(hydroxymethyl)aminomethane (tris) buffer, pH 8.5, and $10^{-3}$ M (ethylenedinitrilo)tetraacetic acid, dipotassium salt (K$_2$EDTA). The aforementioned enzyme solution contained per ml of deionized water: 2.5 mg lysozyme, 1 mg bovine pancreatic deoxyribonuclease, and 1 mg bovine pancreatic ribonuclease. The amount of cell suspension was adjusted to give a final optical density of about 1.0, and the final volume was made to 2.0 ml with tris buffer. The suspension was shaken in a water bath at 37° C. for 20 minutes. The cell debris was removed by centrifugation at 27,000 xg in a refrigerated centrifuge, and the supernatant was assayed for enzyme activity as described in Example 2 above.

Various compounds were evaluated as a carbon source for the aqueous nutrient medium used as the production medium in the above-described test procedure. Each of the aqueous nutrient media tested as a production medium in this example were identical to the above-referenced CFM medium (containing yeast extract but free from agar), except that the carbon source was replaced by the particular compound set forth as shown hereinafter in Table II-A. A series of aqueous media were tested for each different carbon source shown in Table II-A to determine the optimum concentration of each carbon source. Optimum concentration was determined on the basis of that concentration which produced the highest creatinine iminohydrolase activity. The series of media for each carbon source tested was compared to a control medium containing as the carbon source 1.0 wt% fumaric acid. Thus, dry cell weight and creatinine iminohydrolase activity for each carbon source tested in Table II-A were determined as a percentage relative to that of the fumaric acid control for that series. As shown in Table II-A, glycerol, sucrose, acetic acid, and glycine did not support the growth of the culture or produce a detectable amount of enzyme. In the case of aspartic and glutamic acids, representing amino acids, the culture grew well but these sources repressed enzyme synthesis. In contrast to the foregoing carbon sources, acceptable levels of cell growth and enzyme production were obtained from those media employing as the carbon source an indirect amino acid precursor such as lactic acid, malic acid, citric acid, or succinic acid. As further shown in Table II-A the direct amino acid precursor, namely, pyruvic acid supported good enzyme production although somewhat lower cell growth was obtained. Fumaric acid, a direct amino acid precursor and the control used in Table II-A, also yielded good enzyme production and good cell growth of the microorganism. α-Ketoglutaric acid appeared to provide best results as it provided good cell growth of the microorganism and produced more than twice as much enzyme as did the fumaric acid control. These results demonstrated that indirect amino acid precursors served as useful carbon sources, while direct amino acid precursors such as fumaric acid, α-ketoglutaric acid, and pyruvic acid, served as even better carbon sources with α-ketoglutaric acid providing exceptional results.

TABLE II-A

Effect of Carbon Source

| Carbon Source | Optimum Concentration Wt. % | Dry Cell Wt. % of Control | Creatinine Iminohydrolase Activity % of Control |
|---|---|---|---|
| Fumaric Acid[a] | 1.0 | 100 | 100 |
| Glycerol | 0.5 | 18 | — |
| Sucrose | 0.5 | 16 | — |
| Acetic Acid | 0.1 | 16 | — |
| Lactic Acid | 0.5 | 83 | 80 |
| Pyruvic Acid | 0.5 | 71 | 105 |
| Citric Acid | 1.0 | 76 | 71 |
| Succinic Acid | 1.0 | 60 | 49 |
| Malic Acid | 1.0 | 74 | 100 |
| α-Ketoglutaric Acid | 1.0 | 104 | 205 |
| Aspartic Acid | 1.0 | 96 | — |
| Glutamic Acid | 1.0 | 117 | — |
| Alanine | 1.0 | 64 | 35 |
| Glycine | 0.5 | 7 | — |

—: Below the detection limit of creatinine iminohydrolase assay of 20 U/liter.
[a]Fumaric acid (1.0%) was used as control.

EXAMPLE 4

Dry Chemistry Multilayer Analytical Element for Determination of Serum Creatinine In this example, a dry chemistry analytical element for assay of serum creatinine was prepared and evaluated. The element had a multilayer structure of the type illustrated in FIG. 1 of U.S. Pat. No. 4,066,403, including a barrier composition for selectively removing liquid base while permitting passage of ammonia gas to an underlying indicator layer containing a chromogenic ammonia detector. The specific structure of this multilayer element is shown below:

---
Reflecting-Spreading Layer
Polymeric Subbing Layer 1
Creatinine Iminohydrolase Layer
Polymeric Subbing Layer 2
Barrier Layer
Ammonia Detector Layer
Transparent Film Base Support
---

The composition of the reflecting-spreading layer, polymeric subbing layers 1 and 2, the barrier layer, and the support of the above-noted analytical element were the same or quite similar to that of the multilayer analytical element described in detail in Example 4 of U.S. Pat. No. 4,066,403. The creatinine iminohydrolase layer of the above-noted analytical element was composed of a gelatin layer buffered at a pH of 8.5–9.5 containing deionized gelatin as binder at 10.8 g/m$^2$; bis-vinylsulfonyl methane as hardener at 0.05 g/m$^2$; urease-free creatinine iminohydrolase at 3500 U/m$^2$; a buffer composition containing tris(hydroxymethyl)aminomethane-phosphate at 0.07 g/m$^2$, KH$_2$PO$_4$ at 0.08 g/m$^2$, and boric acid at 2.5 g/m$^2$; Triton X-301 (Rohm & Haas Co.) a sodium salt of an alkylaryl polyether sulfate as surfactant at 0.06 g/m$^2$; and glycerol as enzyme stabilizer at 0.54 g/m$^2$. The ammonia detector layer of the above-noted analytical element contained cellulose acetate as binder at 6.5 g/m$^2$, bromophenol blue as ammonia detector at 0.27 g/m$^2$, and a polymeric mordant, poly[styrene-co-(vinylbenzyl)-(trihexyl)-co-ammonium chloride], for the dye at 0.27 g/m$^2$. The above-noted element was evaluated as an analytical test element for serum creatinine as follows:

A series of calibrator fluids formulated from frozen, pooled human serum having creatinine concentrations of 0.05 mg/dl, 1.0 mg/dl, 2.0 mg/dl, 4.0 mg/dl, 8.0 mg/dl, and 16 mg/dl, respectively, were prepared. Ten microliters of each calibrator fluid was then spotted onto a series of identical analytical elements having the structure and composition described in this example, one 10 microliter drop sample of calibrator fluid per element. Each element was then incubated at 37° C., 50% relative humidity for 5 minutes. Thereafter, the optical density developed in the ammonia detector layer was measured by reflection spectrophotometry through the transparent support of each element. The results are shown in Table III below:

TABLE III

| Calibrator Creatinine Concentration (mg/dl) | Reflection Optical Density in Multilayer Creatinine Element at 600 nm |
|---|---|
| 0.05 | 0.61 |
| 1.0 | 0.64 |
| 2.0 | 0.70 |
| 4.0 | 0.80 |
| 8.0 | 1.03 |
| 16.0 | 1.48 |

When the above-noted values in Table III are plotted graphically, one obtains a nearly linear creatinine calibration curve showing $D_R$ (reflection optical density developed in the multilayer element) as a function of serum creatinine concentration.

EXAMPLE 5

Each of the calibrator fluids described in Example 4 was assayed for creatinine concentration using the multi-layer analytical element described in Example 4 and each of these calibrator fluids was also assayed by a high pressure liquid chromatography reference procedure. The results illustrated in Table IV below show that a serum creatinine assay composition and analytical element of the present invention provides analytical results nearly identical to that obtained by the reference procedure.

TABLE IV

| Creatinine Concentration by Reference Procedure (mg/dl) | Creatinine Concentration by Multilayer Analytical Element of Example 4 (mg/dl) |
|---|---|
| 0.05 | 0.043 |
| 1.045 | 1.004 |
| 2.135 | 2.14 |
| 4.17 | 4.11 |
| 8.3 | 8.40 |
| 16.65 | 16.63 |

EXAMPLE 6

In this Example, the eight creatinine desimidase-producing microorganisms listed in U.S. Pat. Nos. 4,087,329 and 4,134,793 were tested to determine whether or not the creatinine disimidase which can be produced from these microorganisms is, in its crude, unpurified form, substantially free of urease activity. Specifically, these eight microorganisms were grown in the medium described in Example 1 of the aforementioned '329 patent as set forth hereinafter in Table V. The procedure used for the cultivation of the microorganisms was the same as in Example 6 of the '329 patent as set forth in Table VI hereinafter. Thereafter, the cells of each of the eight microorganisms were harvested by centrifugation at 1500 xg for 15 minutes in a refrigerated centrifuge. The cell pellet thus obtained from centrifuging 50 ml of fermentation broth was resuspended in 10 ml of 0.1 M potassium phosphate buffer pH 7.5 and was sonicated for 5 minutes to extract enzyme produced within the microbial cells. Cell debris was removed by centrifugation at 27000 xg for 15 minutes in a refrigerated centrifuge. The resultant crude, unpurified enzyme-containing supernatants obtained from each of the eight microorganisms were checked in the manner described hereinabove in Example 2A to see if they exhibited creatinine iminohydrolase activity. In addition, each of the crude, unpurified enzyme-containing supernatants was tested as described hereinabove in Example 2B for urease activity. As a control, the urease-free creatinine iminohydrolase producing microorganism ATCC 31,546 described in the present specification was grown in the CFM medium described hereinabove in Example 1. Cells were harvested and a crude enzyme preparation was extracted from this microorganism in the manner described above with respect to the eight microorganisms of U.S. Pat. No. 4,087,329.

The results of the foregoing comparative tests are set forth in Table VII hereinafter. As noted, each of the microorganisms tested produced a crude enzyme preparation having creatinine iminohydrolase activity. However, except for the control enzyme preparation extracted from the microorganism ATCC 31,546 described in the present specification, none of these crude enzyme preparations were free of urease activity. Moreover, as noted in Table VII, each of the crude enzyme preparations obtained from the microorganisms described in the '329 and the '793 patents exhibited a urease activity which was nearly as great (i.e., at least 75%) or greater than its level of creatinine iminohydrolase activity.

TABLE V

| Culture Medium | Per Liter |
|---|---|
| Glucose | 20.0 g |
| Creatinine Hydrochloride | 5.0 g |
| K$_2$HPO$_4$ | 1.0 g |
| MgSO$_4$ . 7H$_2$O | 0.5 g |
| KCl | 0.5 g |
| Yeast Extract | 1.0 g |
| Adjust pH to 7.5 and make to 1 liter with distilled water. | |

TABLE VI

| Cultivation Conditions | |
|---|---|
| Condition | Description |
| Volume of Medium | 25 ml in 250-ml Erlenmeyer flask |
| Temperature | 30° C. |
| Shaker Speed | 200 rpm |
| Duration | 24 hours |

TABLE VII

Production of Creatinine Iminohydrolase and Urease Activity

| Microorganism | Creatinine Iminohydrolase Production | Urease Activity (U/Liter) |
|---|---|---|
| *Brevibacterium ammoniagenes* ATCC 31169 | Yes | * |
| *Brevibacterium divaricatum* ATCC 14020 | Yes | * |
| *Corynebacterium lilium* ATCC 15990 | Yes | * |
| *Corynebacterium glutamicum* ATCC 31170 | Yes | * |
| *Pseudomonas ovalis* ATCC 31171 | Yes | * |
| *Pseudomonas cruciviae* ATCC 31172 | Yes | * |
| *Arthrobacter ureafaciens* ATCC 7562 | Yes | ** |
| *Arthrobacter histidinolovorans* ATCC 11442 | Yes | * |
| *Flavobacterium filamentosum* ATCC 31546 (Control) | Yes | 0.0 (not detectable) |

*Each microorganism designated by a single asterick produced a crude enzyme preparation having an urease activity (as measured in Units/liter) equal to or greater than its level of creatinine iminohydrolase activity (as measured in Units/liter).
**Each microorganism designated by a double asterick produced a crude enzyme preparation having an urease activity (as measured in Units/liter) equal to 75% or more of the its level of creatinine iminohydrolase activity as measured in Units/liter).

The invention has been described in detail with particular reference to certain preferred embodiments thereof, but it will be understood that variations and modifications can be effected within the spirit and scope of the invention.

What is claimed is:

1. A urease-free creatinine iminohydrolase enzyme preparation derived from an aerobic soil microorganism.

2. A urease-free creatinine iminohydrolase enzyme preparation as described in claim 1 wherein said enzyme has a molecular weight in the range of from about 250,000 to 300,000; a maximum activity at a pH between 7 and 8 as measured at 37° C.; a K$_m$ of about 3 to 5 mM for creatinine as measured at 37° C., pH 7.5; and a specific activity for creatinine of at least about 1.0 unit per milligram of protein in said preparation as measured at 37° C., pH 7.5.

3. A urease-free creatinine iminohydrolase enzyme preparation obtained from the aerobic soil microorganism ATCC 31,546.

4. A freeze-dried powder comprising the urease-free creatinine iminohydrolase enzyme preparation as defined in claim 1, 2 or 3.

5. A method of producing a urease-free creatinine iminohydrolase enzyme comprising the steps of growing the aerobic soil microorganism ATCC 31,546 in an aqueous nutrient medium at a pH in the range of from about 5 to 10, and extracting the enzyme from the microorganism, said nutrient medium comprising:
 (i) a carbon source comprising an amino acid precursor representing an organic acid free from amino groups,
 (ii) a nitrogen source comprising creatinine,
 (iii) trace nutrients, and
 (iv) a buffer.

6. A method of producing a urease-free creatinine iminohydrolase enzyme as described in claim 5 wherein said microorganism is grown in said medium at a temperature within the range of from about 20° to 37° C.

7. A method of producing a urease-free creatinine iminohydrolase enzyme as defined in claim 5 or 6 wherein said carbon source of said nutrient medium comprises a direct amino acid precursor.

8. A method of producing a urease-free creatinine iminohydrolase enzyme as defined in claim 5 or 6 wherein said carbon source of said nutrient medium comprises an amino acid precursor selected from the group consisting of fumaric acid, pyruvic acid, malic acid, and α-ketoglutaric acid.

9. A method of producing a urease-free creatinine iminohydrolase enzyme as defined in claims 5 or 6 wherein said carbon source of said nutrient medium comprises fumaric acid.

10. A method of producing a urease-free creatinine iminohydrolase enzyme as defined in claims 5 or 6 wherein said carbon source of said nutrient medium comprises α-ketoglutaric acid.

11. A method for the determination of creatinine contained in an aqueous liquid which comprises contacting said liquid and a urease-free creatinine iminohydrolase enzyme preparation derived from an aerobic soil microorganism at a pH and temperature effective for said preparation to interact with creatinine and produce detectable amounts of ammonia corresponding to the presence and/or concentration of creatinine.

12. A method for the determination of creatinine contained in an aqueous liquid which comprises contacting said liquid and a urease-free creatinine iminohydrolase enzyme preparation derived from an aerobic soil microorganism at a pH and temperature effective for said preparation to interact with creatinine and produce detectable amounts of ammonia corresponding to the presence and/or concentration of creatinine; said creatinine iminohydrolase enzyme having a molecular weight in the range of from about 250,000 to 300,000; a maximum activity at a pH between 7 and 8 as measured at 37° C.; a $K_m$ of about 3 to 5 mM for creatinine as measured at 37° C., pH 7.5; and a specific activity for creatinine of at least about 1.0 unit per milligram of protein in said preparation as measured at 37° C., pH 7.5.

13. A method for the determination of creatinine in an aqueous liquid as defined in claim 11 or 12 wherein said enzyme preparation is derived from the aerobic soil microorganism ATCC 31,546.

14. A method for the determination of creatinine in an aqueous liquid as defined in claim 11 or 12 wherein said pH and temperature are within the ranges of from about 6 to 10 and about 25° to 40° C., respectively.

15. A method for the determination of creatinine in an aqueous liquid as defined in claim 11 or 12 wherein said aqueous liquid is serum.

16. An assay composition for the determination of creatinine in a liquid, said composition comprising a urease-free creatinine iminohydrolase enzyme preparation derived from an aerobic soil mircroorganism and an ammonia detector.

17. An assay composition for the determination of creatinine in a liquid, said composition comprising a urease-free creatinine iminohydrolase enzyme preparation derived from an aerobic soil microorganism and an ammonia detector, said creatinine iminohydrolase enzyme having a molecular weight in the range of from about 250,000 to 300,000; a maximum activity at a pH between 7 and 8 as measured at 37° C.; a $K_m$ of about 3 to 5 mM for creatinine as measured at 37° C., pH 7.5; and a specific activity for creatinine of at least about 1.0 unit per milligram of protein in said preparation as measured at 37° C., pH 7.5.

18. An assay composition for the determination of creatinine as defined in claim 16 or 17 wherein said enzyme preparation is derived from the aerobic soil microorganism ATCC 31,546.

19. An assay composition for the determination of creatinine as defined in claim 16 or 17 wherein said ammonia detector comprises a chromogenic base indicator.

20. An assay composition for the determination of creatinine as defined in claim 16 or 17 wherein said ammonia detector comprises a base-activatable chromogen containing a protonated dye.

21. An assay composition for the determination of creatinine as defined in claim 16, or 17 wherein said ammonia detector comprises a chromogenic ammonia specific indicator.

22. An assay composition for the determination of creatinine as defined in claim 16 or 17 wherein said ammonia detector comprises an ammonia specific electrode.

23. A method for the determination of creatinine contained in an aqueous liquid which comprises:
 (a) contacting said liquid and an assay composition at a pH and temperature effective for said composition to interact with creatinine and produce detectable amounts of ammonia corresponding to the pressure and/or concentration of creatinine, said assay composition comprising a urease-free creatinine iminohydrolase enzyme preparation derived from an aerobic soil microorganism and an ammonia detector which undergoes a detectable change in response to said ammonia, and
 (b) detecting said change.

24. A method for the determination of creatinine contained in an aqueous liquid which comprises:
 (a) contacting said liquid and an assay composition at a pH and temperature effective for said composition to interact with creatinine and produce detectable amounts of ammonia corresponding to the pressure and/or concentration of creatinine, said assay composition comprising a urease-free creatinine iminohydrolyse enzyme preparation derived from an aerobic soil microorganism and an ammonia detector which undergoes a detectable change in response to said ammonia, said creatinine iminohydrolase enzyme having a molecular weight in the range of from about 250,000 to 300,000; a maximum activity at a pH between 7 and 8 as measured at 37° C., pH 7.5; and a specific activity for creatinine of at least about 1.0 unit per milligram of protein in said preparation as measured at 37° C., pH 7.5, and (b) detecting such change.

25. A method for the determination of creatinine contained in an aqueous liquid as defined in claim 23 or 24 wherein enzyme preparation is derived from the aerobic soil microorganism ATCC 31,546.

26. A method for the determination of creatinine contained in an aqueous liquid as defined in claim 23 or 24 wherein said ammonia detector comprises a chromogenic base indicator.

27. A method for the determination of creatinine contained in an aqueous liquid as defined in claim 23 or 24 wherein said ammonia detector comprises a base-activatable chromogen containing a protonated dye.

28. A method for the determination of creatinine contained in an aqueous liquid as defined in claim 23 or 24 wherein said ammonia detector comprises bromophenol blue.

29. A method for the determination of creatinine contained in an aqueous liquid as defined in claim 23 or 24 wherein said ammonia detector comprises a chromogenic ammonia specific indicator.

30. A method for the determination of creatinine contained in an aqueous liquid as defined in claim 23 or 24 wherein said ammonia detector comprises an ammonia specific electrode.

31. A method for the determination of creatinine contained in an aqueous liquid also containing free ammonia, said method comprising:

(a) treating a first sample of the aqueous liquid to be assayed with an ammonia detector to produce a detectable change corresponding to the amount of free ammonia contained in the sample, and (b) treating a second sample of said aqueous liquid with an assay composition at a pH and temperature effective for said composition to interact with creatinine and produce detectable amounts of ammonia corresponding to the presence and/or concentration of creatinine, said assay composition comprising a urease-free creatinine iminohydrolase enzyme preparation derived from an aerobic soil microorganism and an ammonia detector which undergoes a detectable change in response to ammonia, thereby producing a detectable change corresponding to the amount of free ammonia in said second sample and the amount of ammonia generated by said creatinine iminohydrolase from said second sample, whereby the amount of ammonia produced in step (b) connected for that produced in step (a) corresponds essentially only to that derived from the creatinine present in said aqueous liquid.

32. A method for the determination of creatinine in an aqueous liquid as defined in claim 31 wherein said creatinine iminohydrolase enzyme has a molecular weight in the range of from about 250,000 to 300,000; a maximum activity at a pH between 7 and 8 as measured at 37° C.; a $K_m$ of about 3 to 5 mM for creatinine as measured at 37° C., pH 7.5; and a specific activity for creatinine of at least about 1.0 unit per milligram of protein in said preparation as measured at 37° C., pH 7.5.

33. A method for the determination of creatinine in an aqueous liquid as defined in claim 31 wherein said creatinine iminohydrolase is obtained from the aerobic soil microorganism ATCC 31,546.

34. An element for the determination of creatinine contained in an aqueous liquid, said element having a reagent zone comprising a urease-free creatinine iminohydrolase enzyme preparation as defined in claim 1, 2 or 3.

35. An element for the determination of creatinine in an aqueous liquid, said element having a dry reagent zone comprising a urease-free creatinine iminohydrolase enzyme preparation as defined in claim 1, 2 or 3, an ammonia detector zone comprising as an ammonia detector a chromogenic base indicator, and a barrier zone permeable to ammonia but impermeable to other liquid bases, said barrier zone interposed between said reagent zone and said ammonia detector zone.

36. An analytical element for the determination of creatinine contained in an aqueous liquid, said element comprising a spreading zone to distribute a sample of said aqueous liquid; a dry reagent zone permeable to said sample, said reagent zone containing a urease-free creatinine iminohydrolase enzyme preparation as described in claim 1, 2 or 3; a barrier zone permeable to ammonia but impermeable to other liquid bases; and an ammonia detector zone comprising a chromogenic base indicator; said barrier zone interposed between said reagent zone and said ammonia detector zone.

37. An analytical element for the determination of creatinine contained in an aqueous liquid, said element comprising a support bearing a multilayer structure comprising, in layer order furthest from said support, a spreading layer to distribute a sample of said aqueous liquid, a dry reagent layer permeable to said sample and containing a urease-free creatinine iminohydrolase enzyme preparation as described in claim 1, 2 or 3, a barrier layer selectively permeable to ammonia, and an ammonia detector layer containing as an ammonia detector a chromogenic base-sensitive indicator.

38. An analytical element for the determination of creatinine contained in an aqueous liquid, said element comprising a support bearing a multilayer structure comprising, in layer order furthest from said support, a spreading layer to distribute a sample of said aqueous liquid, a dry reagent layer permeable to said sample and containing a urease-free creatinine iminohydrolase enzyme preparation as described in claim 1, 2 or 3, a barrier layer selectively permeable to ammonia, and an ammonia detector layer containing as an ammonia detector a base-activatable chromogen comprising a protonated dye.

* * * * *